United States Patent
Shrikhande et al.

(10) Patent No.: US 6,403,629 B2
(45) Date of Patent: Jun. 11, 2002

(54) HETEROCYCLIC COMPOUNDS FOR THERAPEUTIC USE

(75) Inventors: Atul Anant Shrikhande; Madhukant Mansukhlal Doshi; Shirish Bhagwanlal Mody, all of Maharashtra (IN)

(73) Assignee: J.B. Chemical and Pharmaceuticals Limited, Maharashtra (IN)

( * ) Notice: Subject to any disclaimer, the term of this patent is extended or adjusted under 35 U.S.C. 154(b) by 0 days.

(21) Appl. No.: 09/809,485

(22) Filed: Mar. 15, 2001

Related U.S. Application Data

(60) Provisional application No. 60/201,343, filed on May 2, 2000, and provisional application No. 60/216,273, filed on Jul. 6, 2000.

(51) Int. Cl.[7] ............... A61K 31/415; C07D 231/12
(52) U.S. Cl. ..................... 514/406; 548/377.1
(58) Field of Search ............ 548/377.1; 514/406

(56) References Cited

U.S. PATENT DOCUMENTS 5,760,068 A * 6/1998 Talley et al. ............ 514/403

OTHER PUBLICATIONS

De Vleeschauwer et al., Chemical Abstracts, 127:33930, 1997.*
Penning et al., J. Med. Chem., 1997, 10, 1347–1365.*

* cited by examiner

Primary Examiner—Fiona T. Powers
(74) Attorney, Agent, or Firm—J. Harold Nissen; Lackenbach Siegel

(57) ABSTRACT

A class of compounds particularly diaryl pyrazole of general formulas 1 and 2 where R and R' represents alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-arylsulfamyl, cyanoamido, amino, amidino, N-monoalkylamido, N-monoarylamido, N,N-dialkylamido, N-alkyl-N-arylamido, N,N-dialkylsulfamyl with the alkyl, or alkyl part of each such group containing 1–3 carbon atoms or mixtures thereof optionally their salts when they exist, and preparation thereof.

The compounds of the present invention are antiinflammatory, antipyretic, antirheumatic, antiosteoarthritic agents with antibacterial activity.

The particular class of compounds is given below (Formula 1 and Formula 2).

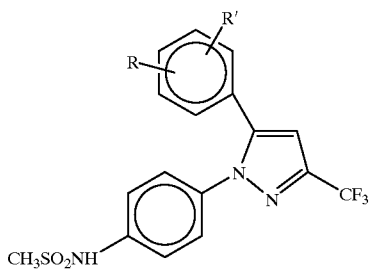

FORMULA 1

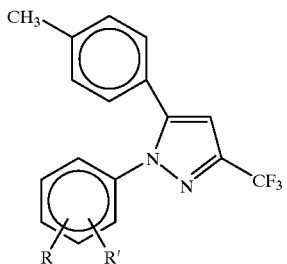

FORMULA 2

18 Claims, No Drawings

HETEROCYCLIC COMPOUNDS FOR THERAPEUTIC USE

RELATED APPLICATION

This application claims priority to provisional application Ser. Nos. 60/201,343 filed May 2, 2000 and 60/216,273 filed on Jul. 6, 2000.

FIELD OF INVENTION

The present invention relates to new heterocyclic compounds of the general formula 1 and 2 for therapeutic use.

The invention further relates to pharmaceutical compositions containing the compounds of the general formula 1 and 2, process for preparing the same and pharmaceutically acceptable salts thereof having a selective action on inflammation and its related disorders.

BACKGROUND OF THE INVENTION

Nonsteroidal anti-inflammatory drugs (NSAIDS) are compounds used mainly in the relief of pain, inflammation, and sometimes fever.

The combined analgesic and antiinflammatory effects of NSAIDS make them particularly useful for the symptomatic relief of painful and/ or inflammatory conditions including musculoskeletal and joint disorders, such as rheumatoid arthritis, osteoarthritis, spondylo arthopathic, peri-articular and soft tissue disorder.

NSAIDS have shown to be useful in alleviating symptoms of inflammation and pain disorders. Prostaglandins (PGs) are ubiquitous fatty acid derivatives that serve as autocrine/paracrine mediators involved in many different physiological processes in addition to their well recognized role in inflammation and immune response modulation. Prostaglandins elicit a variety of important and beneficial responses. Among the undesirable properties of Prostaglandins is their ability to induce pain, fever, and symptoms associated with the inflammatory response.

NSAIDS exert their actions primarily by inhibiting the production of PGs. Recent studies of inflammatory processes has led to the identification of the key enzyme cycloxygenase (Cox) that is expressed in inflammatory conditions. Various studies on the identification of Cox-2 enzyme are reported:-Vane, J. R.; Nature 1994, Made, E. A. ., Smith W. L. ., Dewitt, D. L. J. Biol. Chem. 1993, 268: 6610–14

Cox is the first enzyme in the prostanoid biosynthetc pathway catalyzing the conversion of arachidonic acid to PGH2 as the first step in the synthesis of PGs, Prostacyclins, and Thromboxane, all of which act as important mediators of biological and inflammatory responses. Pairet, M., Engekelhardt,G; Fundam . Clin. Pharmacol 1996, 10, 1–15

The discovery of second inducible isoenzyme has enabled the identification of two major isoforms of COX: the constitutive COX isoform, termed Cox-1 and the inducible isoform, termed the Cox-2 There are now various theories supporting the fact that the inducible Cox-2 enzyme is responsible for the production of inflammatory mediators. Drugs of Future 1998, 23, 598–601.

The commonest side effects occurring during therapy with NSAIDS are generally gastrointestinal disturbances, these are usually mild and reversible but in some patients, peptic ulcer and severe gastrointestinal bleeding have been reported. These adverse effects on the gastrointestinal tract may be associated with the inhibition of the form of cyclooxygenase-1 (Cox-1). NSAIDS that are highly selective inhibitors of the form cycloxygenase-2 ( Cox-2) may have less gastrointestinal toxicity, hence, interest has developed in NSAIDS that are highly selective inhibitors of Cox-2, such as Meloxicam; Nimesulide, Rofecoxib and the like.

Most widely used NSAIDS like Diclofenac, Flufenamic acid, Ibuprofen, Indomethacin and the like, inhibit both the forms of the enzymes (Cox-1 and Cox-2) with many showing selectivity for Cox-1 enzyme.

Inhibition of COX-1 enzyme causes the common gastrointestinal side effects as seen in the known NSAIDS like Diclofenac, Flufenamic acid, Ibuprofen, Indomethacin and the like. All these antiinflammatory agents have shown undesirable side effects.

OBJECT OF THE INVENTION

It is an object of the present invention to provide new pyrazole derivatives and their pharmaceutical compositions as well as their therapeutic uses and the processes for preparing the same. At present there is a pharmacoepial dogma establishing a mandatory connection between anti-inflammatory, antipyretic, other therapeutic uses and the side effects mainly, gastrointestinal disturbances caused by the known NSAIDS. This dogma and the constant need has instigated the inventors to develop a newly synthesized anti-inflammatory compounds showing antimicrobial and antipyretic activity with less side effects. The pyrazole class has shown a promising drug like Celecoxib. The description of various pyrazole derivatives has been disclosed in U.S. Pat. No. 5,521207, J. Med. Chem. 1997, 40, 1347–1365

Pyrazoles have been described for use in the treatment of inflammation U.S. Pat. No. 5,134,142 to Matsuo et al describes 1,5-diaryl pyrzoles and specifically, 1-(4-fluorophenyl)-5-[4-(methylsulfonyl)phenyl]-3-trifluoromethyl pyrazole, as having anti inflammatory activity.

In view of the extensive studies on the above derivatives, the inventors have discovered new compounds of diarylpyrazole class having more advantageous properties and the manufacturing process for the said new pyrazole derivatives fulfilling the desirable features as described herein under.

DESCRIPTION OF THE INVENTION

The present invention relates to new NSAIDS compounds having Diarylpyrazole ring of the general formula 1 and formula 2, their synthesis and their pharmaceutically acceptable addition salts having a antiinflammatory, antipyrefic, or antibacterial activity.

The present invention also relates to synthesis of the intermediates (substituted diketo compounds ) of the compounds of general formula 1:

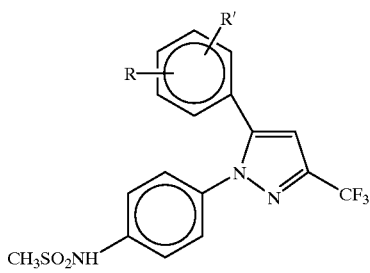

FORMULA 1 where R and R' represents alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-aryl sulfamyl, cyanoamido, amino, amidino, N-monoalkylamido, N-monoarylamido, N,N-dialkylamido, N-alkyl-N-aryl amido, N,N-dialkylsulfamyl with the alkyl or alkyl part of each such group containing 1-3 carbon atoms.

The following diarylpyrazole compounds of the formula I and their pharmaceutically acceptable salts and the corresponding appropriately substituted intermediates for condensation is given below:

1) N-[4-[5-(4-Methylphenyl)-3-(trifluoromethyl)-1H-pyrazol-1-yl]phenyl]methanesulphonamide prepared by condensation of 4-(methanesulphonamido) phenylhydrazine hydrochloride and 1-(4-Methylphenyl)-4,4,4-trifluorobutane-1,3-dione.

1A) N-[4-[5-(4-Ethylphenyl)-3-(trifluoromethyl)-1H-pyrazol-1-yl]phenyl]methanesulphonamide prepared by condensation of 4-(methanesulphonamido) phenylhydrazine hydrochloride and 1-(4-Ethylphenyl)-4,4,4-trifluorobutane-1,3-dione 1B) N-[4-[5-(4-Methoxyphenyl)-3-(trifluoromethyl)-1H-pyrazol-1-yl]phenyl]methanesulphonamide prepared by condensation of 4-(methanesulphonamido) phenylhydrazine hydrochloride and 1-(4-Methoxyphenyl)-4,4,4-trifluorobutane-1,3-dione 1C) N-[4-[5-(4-Ethoxyphenyl)-3-(trifluoromethyl)-1H-pyrazol-1-yl]phenyl]methanesulphonamide prepared by condensation of 4-(methanesulphonamido) phenylhydrazine hydrochloride and 1-(4-Ethoxyphenyl)-4,4,4-trifluorobutane-1,3-dione 1D) N-[4-[5-(3,4-Dichlorophenyl)-3-(trifluoromethyl)-1H-pyrazol-1-yl]phenyl]methanesulphonamide prepared by condensation of 4-(methanesulphonamido) phenylhydrazine hydrochloride and 1-(3,4-Dichlorophenyl)-4,4,4-trifluorobutane-1,3-dione 1E) N-[4-[5-(2,4-Dichlorophenyl)-3-(trifluoromethyl)-1H-pyrazol-1-yl]phenyl]methanesulphonamide prepared by condensation of 4-(methanesulphonamido) phenylhydrazine hydrochloride and 1-(2,4-Dichlorophenyl)-4,4,4-trifluorobutane-1,3-dione 1F) N-[4-[5-(2-Methylphenyl)-3-(trifluoromethyl)-1H-pyrazol-1-yl]phenyl]methanesulphonamide prepared by condensation of 4-(methanesulphonamido) phenylhydrazine hydrochloride and 1-(2-Methylphenyl)-4,4,4-trifluorobutane-1,3-dione 1G) N-[4-[5-(2,4-Dimethylphenyl)-3-(trifluoromethyl)-1H-pyrazol-1-yl]phenyl]methanesulphonamide prepared by condensation of 4-(methanesulphonamido) phenylhydrazine hydrochloride and 1-(2,4-Dimethylphenyl)-4,4,4-trifluorobutane-1,3-dione 1H)

N-[4-[5-(3,4-Dimethylphenyl)-3-(trifluoromethyl)-1H-pyrazol-1-yl]phenyl]methanesulphonamide prepared by condensation of 4-(methanesulphonamido) phenylhydrazine hydrochloride and 1-(3,4-Dimethylphenyl)-4,4,4-trifluorobutane-1,3-dione 1I) 4-[1-[4-(Methanesulphonamido)phenyl]-3-(trifluoromethyl)-1H-pyrazol-5-yl]benzoic acid prepared by the oxidation of N-[4-[5(4-Methylphenyl)-3-(trifluoromethyl)-1H-pyrazol-1-yl]phenyl] methanesulphonamide 1J) 2-[1-[4-(Methanesulphonamido)phenyl]-3-(trifluoromethyl)-1H-pyrazol-5-yl]benzoicacid prepared by the oxidation of N-[4-[5(2-Methylphenyl)-3-(trifluoromethyl)-1H-pyrazol-1-yl]phenyl] methanesulphonamide The present invention also relates to synthesis of the intermediates (substituted phenyl hydrazine hydrochloride salts) of the compounds of general formula 2:

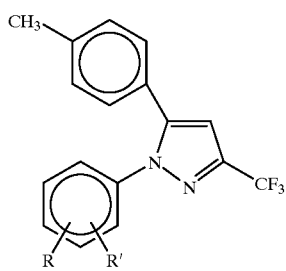

where R and R' represents alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N- aryl sulfamyl, cyanoamido, amino, amidino, N-monoalkylamido, N-monoarylamido, N,N-dialkylamido, N-alkyl-N-aryl amido, N,N-dialkylsulfamyl with the alkyl or alkyl part of each such group containing 1-3 carbon atoms, The following diaryl pyrazole compounds of the formula 2 and their pharmaceutically acceptable salts and the corresponding appropriately substituted intermediates for condensation are given below:

2) 1-(3-Chloro4-fluorophenyl)-5-(4-methylphenyl)-3-(trifluoromethyl)pyrazole can be obtained by condensation of 1-(4-Methylphenyl)-4,4,4-trifluorobutane-1,3-dione with 3-Chloro4-fluorophenylhydrazine hydrochloride 2A) 1-(3-Chlorophenyl)-5-(4-methylphenyl)-3-(trifluoromethyl)pyrazole can be obtained by condensation of 1-(4-Methylphenyl)-4,4,4-trifluorobutane-1,3-dione with 3-Chlorophenylhydrazine hydrochloride 2B) 1-(4-Chlorophenyl)-5-(4-methylphenyl)-3-(trifluoromethyl)pyrazole can be obtained by condensation of 1-(4-Methylphenyl)-4,4,4-trifluorobutane-1,3-dione with 4-Chlorophenylhydrazine hydrochloride 2C) 1-(2,4-Difluorophenyl)-5-(4-methylphenyl)-3-(trifluoromethyl)pyrazole can be obtained by condensation of.1-(4-Methylphenyl)-4,4,4-trifluorobutane-1,3-dione with 2,4-Difluorophenylhydrazine hydrochloride 2D) 1-(3-Fluorophenyl)-5-(4-methylphenyl)-3-(trifluoromethyl)pyrazole can be obtained by condensation of 1-(4-Methylphenyl)-4,4,4-trifluorobutane-1,3-dione with 3-Fluorophenylhydrazine hydrochloride 2E) 1-(4-Fluorophenyl)-5-(4-methylphenyl)-3-(trifluoromethyl)pyrazole can be obtained by condensation of, 1-(4-Methylphenyl)-4,4,4-trifluorobutane-1,3-dione with 4-Fluorophenylhydrazine hydrochloride b 2F) 1-(3,4-Dichlorophenyl)-5-(4-methylphenyl)-3-(trifluoromethyl)pyrazole can be obtained by condensation of 1-(4-Methylphenyl)-4,4,4-trifluorobutane-1,3-dione with 3,4-Dichlorophenylhydrazine hydrochloride 2G) 1-(2-Fluoro4-methylphenyl)-5-(4-methylphenyl)-3-(trifluoromethyl)pyrazole can be obtained by condensation of 1-(4-Methylphenyl)-4,4,4-trifluorobutane-1,3-dione with 2-Fluoro-4-methyl-phenylhydrazine hydrochloride 2H) 1-(2-Fluoro-5-methylphenyl)-5-(4-methylphenyl)-3-(trifluoromethyl)pyrazole can be obtained by condensation of 1-(4-Methylphenyl)-4,4,4-trifluorobutane-1,3-dione with 2-Fluoro-5methylphenylhydrazine hydrochloride 2I) 1-(3-Fluoro4-methylphenyl)-5-(4-methylphenyl)-3-(trifluoromethyl)pyrazole can be obtained by condensation of 1-(4-Methylphenyl)-4,4,4-trifluorobutane-1,3-dione with 3-Fluoro4-methylphenylhydrazine hydrochloride The synthesis of the other compounds of formula 1 and 2 includes the conventional method of condensing the appropriate hydrochloride salt of substituted phenyl hydrazine with substituted triflurobutanedione (diketo compounds). This invention also includes the preparation and purification of the intermediates of the compounds of formula 1 and 2. Also included in this invention is the addition products, derivatives, salts formed from pharmaceutically acceptable acids or bases of the compounds of particular interest. The salts or derivatives may be prepared by conventional methods by reacting the appropriate acid or base with the compounds of the general formula 1 and 2

The present invention also relates to the pharmaceutical compositions consisting of a product of the general formula 1 and 2 or its pharmaceutically acceptable salt when they exist, optionally in combination with any other pharmaceutically compatible substance, which may be inert, or physiologically active.

The compositions according to the invention may be administered in the form parenteral, oral, sublingual rectal, vaginal, topical, transdermal, ocular, or intranasal routes or as aerosol for the lungs.

Such compositions can also be administered in the form of modified release, controlled release, time released formulations and the like.

The term 'parenteral' as used herein enclose subcutaneous injection intravenous intramuscular, intrastemal injection or infusion techniques. The sterile compositions includes aqueous or non aqueous solutions, suspension or emulsions. The vehicles used can be selected from water, propylene glycol, vegetable oil, injectable organic esters or suitable organic solvents. The other adjuvants includes wetting agents, isotonicity agents, emulsifiers and dispersants and stabilizers.

The term 'oral' as used includes a composition containing the non toxic therapeutically effective amount of the compounds of formula 1 and 2 in a form suitable for oral use. Such as tablets, capsules, troches, lozenges, aqueous or oily suspensions, dispersible powder or granules, emulsions syrups, elixirs caplets, chewable waffers and solutions freeze dried for oral or injectable dosage forms.

The term 'rectal' or 'vaginal' includes compositions of the active component in the form of suppositories which is prepared by mixing with non irritant ingredients.

The term 'topical' composition includes compositions like creams ointments, lotions, gels, solutions or suspensions.

The term 'ocular' includes compositions like installations.

The term 'intranasal' includes compositions like drops, spray and the like.

The term 'transdermal' includes compositions of the active component in the form of a patch.

The amount of the active ingredient that may be combined with the carrier materials to produce a single dosage form will vary depending upon the host treated and the particular mode of administration. For example, a formulation intended for the oral administration of humans may contain from 0.5 mg to 5 gms of the active ingredient compounded with an appropriate and convenient amount of carrier material which may vary from about 5 to 95% of the total composition.

General Process for the Preparation of Compounds of Formula 1 and 2

The compounds of the formula 1 and 2 as described in this invention can be synthesized in a known procedure as given in the scheme below

PART A: PREPARATION OF SUBSTITUTED PHENYLHYDRAZINE HYDROCHLORIDE

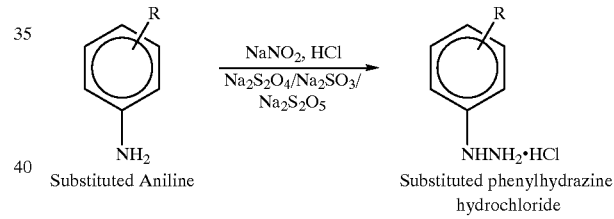

PART B: PREPARATION OF SUBSTITUTED DIKETO COMPOUNDS

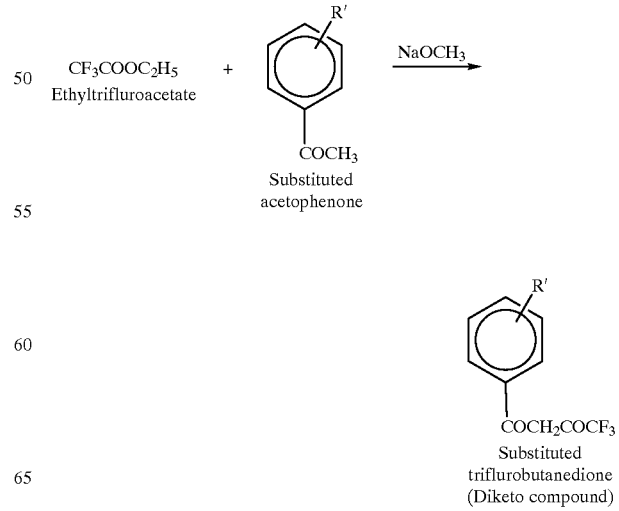

PART C: CONDENSATION

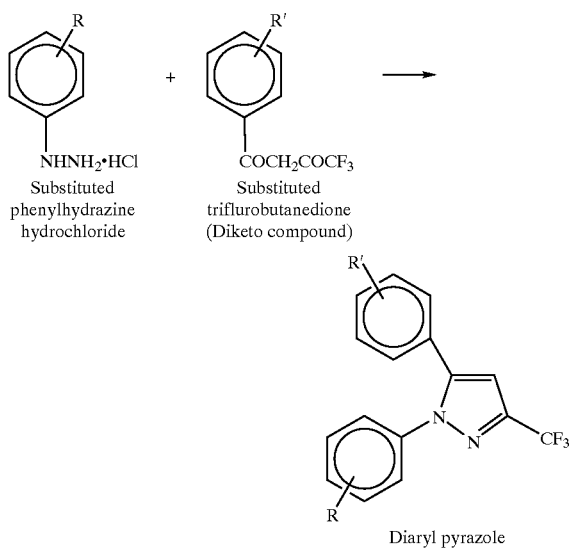

Diaryl pyrazole

The invention will now be illustrated with the aid of following non limiting examples. It should be understood, however, that the invention is not limited to the solely to the particular examples given below. It will be apparent that those skill in the art that any modifications, both to the materials and methods, may be practiced without departing from the purpose and interest of this invention a) all operations carried out at room temperature or ambient temperature were in the range of 18 to 25 degree C.

b) evaporation of the solvent was carried out using a rotary evaporator under reduced pressure (600–4000 pascals;4.5–30mm Hg)with a bath temperature of upto 60 degree C.

c) the course of the reaction was monitored by thin layer chromatography (TLC) and reaction times are given for illustration only.

d) melting points are uncorrected, the melting points are given for the materials prepared as described, polymorphism may result in isolation of materials with different melting points in some preparations.

e) the structure and purity of all final products were assured by at least one of the following techniques: TLC, NMR(nuclear magnetic resonance)spectroscopy, IR(lnfrared spectroscopy), or microanalytical data.

f) yields are given for illustration only.

g) when given, NMR data is in the form of delta (δ)values for major diagnostic protons given in parts per million ( ppm) relative to tetramethylsilane (TMS) as internal standard determined at 300 MHz or 400 MHz using the indicated solvent.

h) When given, IR data is in the form of absorption/cm for characteristic absorption of the compound, determined from 400 to 4000/ cm using Potassium bromide (KBr) disc i) chemical symbols have their usual meanings; the following abbreviations have also been used: v( volume ), w(weight), B.P.( boiling point), M.pt.(melting point), L(liters), ml(milliliters),gms(grams), mg(milligrams), mol (moles), mmol(millimoles) eq (equivalents) deg C (degree centigrade), conc. HCl( concentrated hydrochloric acid)

General Process for the Preparation of Compounds of Formula 1

In the step 1 of the scheme, 4-(methanesulphonamido) phenylhydrazine hydrochloride is prepared by known conventional methods In the step 2,the appropriate acetophenone is treated with the base and a ester to give the intermediate diketo compound. This diketo compound is purified by recrystallisation.

In the step3 , the Hydrazine hydrochloride of step 1 and diketo of step 2 is reacted in solvents for example lower aliphatic alcohols such as methanol, ethanol, Isopropanol and the like and lower aliphatic acids such as acetic acid and the like.

The reaction conditions for diazotisation as in step 1 varies from –10 deg C to +60 deg C The general reaction time for step 2 varies from 8–40 hours and temperature conditions vary from 20 deg C to 60 deg C The reaction conditions for the final condensation as in step 3 varies from 20 deg C to 110 deg C and time period of 6–30 hours.

The recrystallisation solvents includes from lower aliphatic alcohols such as methanol, ethanol, Isopropanol and the like, lower aliphatic hydrocarbons such as hexane, heptane or diethylether or any other suitable inert solvent.

EXAMPLE 1

Preparation of N-[4-[5-(4-Methylphenyl)-3-(trifluoromethyl)-1H-pyrazol-1-yl]phenyl] methanesulphonamide.

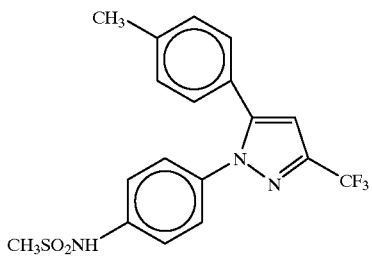

Part A

Preparation of 4-Methanesulphonamido)Phenylhydrazine Hydrochloride 4-(methanesulphonamido)aniline (M.pt :116–118 deg C) was prepared from p-nitroaniline and methanesulphonyl chloride in presence of a base like N,N-dimethylaniline. The resulting 4-(methanesulphonamido)nitrobenzene (M.pt: 180–182 deg C) was then reduced with sodium dithionite under alkaline conditions.

In a 500 ml round bottom flask provided with efficient stirring and external cooling arrangement, 119 ml (1.19 mol) of conc.HCl was cooled to below 5 deg C and 88 gms(0.47 mol) 4-(methanesulphonamido)aniline was added. The hydrochloride thus precipitated was then diazotised below 0 deg C with 33.4 gms (0.48 mol)sodium nitrite dissolved in 50 ml water and the resulting diazonium salt was decomposed with 220 gms (1.15 mol)sodium metabisulphite in 500 ml water. 4-(methanesulphonamido)phenylhydrazine hydrochloride thus precipitated within 30 mins, was filtered and recrystallized from water. The dried product was 76 gms ( yield 68%). M.pt decomposed at 240–242 deg C. IR (KBr) cm–1 3257, 1606 (NH), 1512 (C═C ), 1305 (—SO2NH—), 1127( C═S)

Part B
Preparation of 4-Methylphenyl)-4,4,4-Trifluorobutane-1,3-Dione 125 gms (0.93 mol) of p-Methylacetophenone was dissolved in 250 ml Methanol (anhydrous) and 270 ml of Sodium Methoxide (25% in methanol) was added slowly maintaining the temperature below 30 deg C. The reaction mixture was further diluted with 250 ml Methanol and 128 ml of Ethyltrifluoroacetate(1.0 mol) was added in 4 lots with a in—between stirring period of 5 hours. The reaction was stirred at 20–30 deg C for 16 hours. The reaction mixture was concentrated under vacuum below 40 deg C to 50% and then poured over mixture of 150 ml concentrated Hydrochloric acid and 200 gms ice. The mixture was stirred below 5 deg C for 2 hours and filtered the product was washed with water till neutral pH and suck dried under vacuum 25 gms of p-Methylacetophenone was recovered from the filtrate. The 1-(4-Methylphenyl)-4,4,4-trifluorobutane-1,3-dione was dried under vacuum to give 111 gms off white crystalline product.( 65%) This was further recrystallized from Isopropanol to give 90 gms of white crystals. M.pt 50–52 deg C.

IR KBr cm-1 1064 (C-C), 1147 (C=O), 1199 (CF3), 1458 (C—H), 1608 (aromatic C=O)

Part C
Preparation of N-[4-[5-(4-Methylphenyl)-3-Trifluoromethyl)-1H-Pyrazol-1-Phenyl]Methanesulphonamide.

15 gms (0.065 mol) of 1-(4-Methylphenyl)-4,4,4-trifluorobutane-1,3-dione and 35 gms (0.15 mol) of 4-(methanesulphonamido)phenylhydrazine hydrochloride was refluxed in 150 ml anhydrous glacial acetic acid for 36 hours along with continuous monitoring of the reaction by TLC and then cooled to below 20 deg C and filtered .The residue was washed with hot water till neutral pH. The crude product (16 gms)was recrystallized from Methanol or Methanol and Isopropanol mixture to give 12 gms (46%) bright orange color product (M.pt 186 deg C). The purity was 99.8% by HPLC. Chilling of the mother liquor gave further 3 gms of 99.0% purity by HPLC.

1H NMR CDCl3 (300 MHz):2.1 (s, 1H), 2.4 (.s, 3H), 3.0 ( s, 3H), 7.26 ( m, 2H 7.42 (m, 4H), 7.52 (m, 2H), 9.0 (s, 1H).

IR ( KBr) cm-1 3251 (NH), 1691 (—C=NH), 1525 (C=C), 1481 (CH3), 1325 (Ar—NH—Ar), 1257 (CF3), 1186 (—SO2NH2—), 1141 (C—N).

The following compounds (examples 1A-a to 1H-a) was obtained according to procedures similar to that exemplified in PART B of Example 1.

The appropriate acetophenones were used for the preparation of the diketo intermediates and recrystallized in the similar manner as above:

1A-a) 1-(4-Ethylphenyl)-4,4,4-trifluorobutane-1,3-dione

This intermediate was prepared from commercially available 4-Ethylacetophenone.

The product obtained was a liquid which was isolated from the reaction mixture by extraction with a suitable solvent like Ethylacetate. The evaporation of the solvent gave the diketo compound which was used as such for next step. Yield obtained was 66%.

IR (KBr) cm-1 1228 (C-C), 1149 (aliphatic C=O), 1188 (CF3), 1512 (CH3), 1328(aromatic C=O)

1B-a) 1-(4-Methoxyphenyl)-4,4,4-trifluorobutane-1,3-dione

This intermediate was prepared from commercially available 4-Methoxyacetophenone. The recrystallized product was a light yellow crystalline powder.

Yield obtained was 56%.

M.pt: 57 deg C

IR ( KBr) cm-1 1255 (OCH3), 1110 (C-C), 1139 (aliphatic C=O), 1195 (CF3), 1508 (C—H), 1600 (aromatic C=O)

1C-a) 1-(4-Ethoxyphenyl)-4,4,4-trifluorobutane-1,3-dione

This intermediate was obtained from commercially available 4- Ethoxyacetophenone The recrystallized product was obtained in 48% yield as creamish white crystals.

M.pt: 54 deg C

IR (KBr) cm-1 1271 (C—O—C), 1114 (C-C), 1143 (aliphatic C=O), 1182 (CF3), 1560 (C-H), 1604 (aromatic C=O)

1D-a) 1-(3,4-Dichlorophenyl)-4,4,4-trifluorobutane-1,3-dione

This intermediate was prepared from commercially available 3,4-Dichloroacetophenone The recrystallized product was obtained in 40% yield as a cream powder.

M.pt: 40 deg C

IR (KBr) cm-1 1550 (C-C), 1149 (aliphatic C=O ), 1072 (CF3), 1469(C—H), 1593 (aromatic C=O), 802 (C—Cl)

1E-a) 1-(2,4-pichlorophenyl)-4,4,4-trifluorobutane-1,3-dione

This intermediate was prepared from 2,4- Dichloroacetophenone which is commercially available. The product obtained was a liquid which was isolated by extraction using a suitable organic solvent like Ethylacetate. The evaporation of the solvent gave the diketo product which was used as such for the next step. The yield was 68%.

IR (KBr) cm-1 1551 (C-C), 1150 (aliphatic C=O ), 1120 (CF3), 1480(C—H), 1608 (aromatic C=O ), 810 (C—Cl)

1F-a) 1-(2-Methylphenyl)-4,4,4-trifluorobutane-1,3-dione

This intermediate was prepared from commercially available 2- methylacetophenone. The product obtained was a liquid which was isolated from the reaction mixture by extraction with a suitable solvent like Ethyl acetate. The evaporation of the solvent gave the diketo product in 64% yield which was used as such for the next step.

IR (KBr) cm-1 at 1147 (aliphatic C=O), 1199 (CF3 ), 1458 (C—H) 1608 (aromatic C=O)

1G-a) 1-(2,4-Dimethylphenyl)-4,4,4-trifluorobutane-1,3-dione

This intermediate was prepared from commercially available 2,4-Dimethyl acetophenone. The product obtained was a liquid which was isolated from the reaction mixture by extraction with a suitable solvent like Ethyl acetate. The evaporation of the solvent gave the diketo product in 69% yield which was used as such for the next step.

IR (KBr) cm-1 1170 (aliphatic CSO), 1182 (CF3), 1458 (C—H), 1608 (aromatic C=O)

1H-a) 1-(3,4-Dimethylphenyl)-4,4,4-trifluorobutane-1,3-dione

This intermediate was prepared from commercially available 3,4dimethylacetophenone The recrystallized product was obtained in 48% yield as a pale cream solid.

M.pt: 110 deg C

IR (KBr)cm-1 1093 (C-C), 1170 (aliphatic C=O ), 1182 (CF3 ), 1 458 (C—H), 1608 (aromatic C=O)

The following compounds (examples 1 A to 1 H) was prepared in the similar procedure as exemplified in the Part C of example 1 using the appropriate diketo compounds 1A) N-[4-[5-(4-Ethylphenyl)-3-trifluoromethyl)-1H-pyrazol-1-yl]phenyl]methanesulphonamide.

Yield: 28%

A dark orange powder.

M.pt: 189 deg C

IR (KBr) cm-1 3261 (NH), 1697 (—C=NH), 1512 (C=C), 1402 (CH3) 1371 (Ar—NH—Ar), 1328 (CF3), 1186 (—SO2NH2), 1147 (C—N)

Purity by HPLC: 99.5%

1B) N-[4-[5-(4-Methoxyphenyl)-3-trifluoromethyl)-1H-pyrazol-1-yl]phenyl]methanesulphonamide.

Yield 56%

A dark yellow crystalline powder.

M.pt: 187 deg C

IR (KBr) cm-1 3251 (NH), 1701 (—C=NH), 1510 (C=C), 1336 (Ar—NH—Ar) 1153 (CF3), 1191 (SO2NH2), 1249 (OCH3)

Purity by HPLC: 98.96%

1C) N-[4-[5-(4-Ethoxyphenyl)-3-trifluoromethyl)-1H-pyrazol-1-yl]phenyl]methanesulphonamide.

Yield: 48%

A dark yellow crystalline powder.

M.pt: 164 deg C

IR (KBr) cm-1 3340 (NH), 16.97 (—C=NH), 1512 (C=C), 1253 ( OCH3) 1325( Ar—NH—Ar), 1151 (CF3), 1220 (SO2NH2)

Purity by HPLC: 99.46%

1D) N-[4-[5(3,4-Dichlorophenyl)-3-trifluoromethyl)-1H-pyrazol-1-yl]phenyl]methanesulphonamide.

Yield: 50%

A dark orange yellow powder.

M.pt: 186 deg C

IR (KBr) cm-1 3276 (NH), 1701 ( C=NH), 1510 (C=C), 1371( Ar—NH—Ar), 1226 ( CF3), 1195 (SO2NH2) 1145 (C—N), 815 (C—Cl)

Purity by HPLC: 98.74%

1E) N-[4-[5-(2,4-Dichlorophenyl)-3-trifluoromethyl)-1H-pyrazol-1-yl]phenyl]methanesulphonamide.

Yield : 28%

A dark yellow powder

M.pt: 162 deg C

IR (KBr) cm-1 3278 (NH), 1714 (—C=NH), 1510 (C=C), 1375( Ar—NH—Ar), 1222 (CF3) 1195 (SO2NH2), 1147 (C—N), 995 (C—Cl)

Purity by HPLC: 99.6%

1F) N-[4-[5-(2-Methylphenyl)-3-trifluoromethyl)-1H-pyrazol-1yl]phenyl]methanesulphonamide Yield: 30%

A yellow crystalline powder

M.pt: 175 deg C

Purity by HPLC: 98.5%

IR (KBr) /cm: 3267(N—H), 1703 ( Imine C=NH), 1510 (CH3), 1328 (Ar—NH—Ar) 1244 (CF3), 1190 (SO2NH2), 1157 (C—N)

1G) N-[4-[5-(2,4-Dimethylphenyl)-3-(trifluoromethyl)-1H-pyrazol-1-yl]phenyl]methanesulphonamide.

Yield: 45%

A bright yellow color product.

M.pt: 152 deg C

IR (KBr) cm-1 3278 (NH), 1705 (—C=NH), 1512 (C=C), 1384 (CH3) 1332(Ar—NH—Ar), 1224(CF3) 1191 (SO2NH2), 1153(C—N)

Purity by HPLC : 99.0%

1H) N-[4-[5-(3,4-Dimethylphenyl)-3-(trifluoromethyl)-1H-pyrazol-1-yl]phenyl]methanesulphonamide.

Yield: 36%

A bright red color powder

M.pt:175 deg C

IR (KBr) cm-1 3240(NH), 1701(—C=NH ), 1514 (C=C), 1467 (CH3), 1330(Ar—NH—Ar), 1251 (CF3), 1186 (SO2NH2), 1153 (C—N)

Purity by HPLC: 99.3%

1I) Preparation of 4-[4-(Methanesulphonamido)phenyl]-3-(trifluoromethyl)-1H-pyrazol-5-yl]benzoic acid.

A solution of 3 gms of N-[4-[5-(4-Methylphenyl)-3-trifluoromethyl)-1H-pyrazol-1-yl]phenyl]methanesulphonamide in 10 ml Acetone was stirred at room temperature. Jones reagent ( about 8 ml ) was added dropwise maintaining the room temperature, till the orange color of Jones reagent persisted. The reaction was stirred at room temperature for 6 hours and monitored by TLC. The reaction mixture was concentrated under vacuum and the residue was extracted using a suitable solvent such as Ethylacetate and this extract was washed with water and brine. The organic layer was dried over sodium sulfate and evaporated to give a brown colored product (3 gms) The crude product was recrystallized from Isopropanol to give a pale brown product. M.pt: 168–70 deg C 1J) 2-[1-[4-(Methanesulphonamido)phenyl]-3-(trifluoromethyl)-1H-pyrazol-5-yl]benzoic acid.

N-[4-[5-(2-Methylphenyl)-3-trifluoromethyl)-1H-pyrazol-1-yl]phenyl]methanesulphonamide was prepared by condensation of 4-(methanesulphonamido)phenylhydrazine hydrochloride and 1-(2-Methylphenyl)-4,4,4-trifluorobutane-1,3-dione by the process as described in Part C of Example I This compound was oxidized by Jones reagent as described in Example 2 to give a bright yellow colored solid in 26% yield. M.pt:164–166 deg C General Process for the Preparation of the Compounds of Formula 2

In the step 1, the appropriate phenylhydrazine was obtained from the corresponding primary aromatic amine by diazotisation with sodium nitrite and decomposing the diazonium salt with sodium sulfite and precipitating the hydrazino compound as hydrochloride salt with HCl.

In the step 2, the p-Methyl acetophenone was condensed with Ethyltrifluoroacetate under alkaline conditions to give the 1-(4-Methylphenyl)-4,4,4-trifluorobutane-1,3-dione intermediate.

In the step 3, the Hydrochloride of corresponding hydrazino compounds of step 1 and diketo compound of step 2 is reacted in solvents for example lower aliphatic alcohols such as methanol, ethanol, isopropanol and the like and lower aliphatic acids such as acetic acid and the like.

The reaction conditions for diazotisation as in step 1 varies from −10 deg C to +60 deg C The general reaction time for step 2 varies from 8–40 hours and temperature conditions vary from 20 deg C to 60 deg C The reactions conditions for the final condensation as in step 3 varies from 20 deg C to 110 deg C and time period of 6–30 hours.

The recrystallisation solvents includes from lower aliphatic alcohols such as methanol, ethanol, isopropanol and the like, lower aliphatic hydrocarbons such as hexane, heptane or Diethylether., or any other suitable inert solvent.

EXAMPLE -2
Preparation of 1-Chloro-4-Fluorophenyl)-5-(4-Methylphenyl)-3-(Trifluoromethyl)Pyrazole.

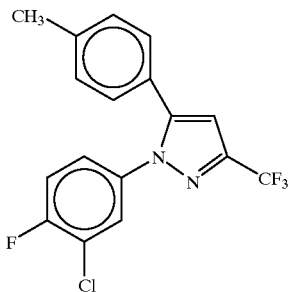

Part A
Preparation of 3-Chloro-4-Fluorophenylhydrazine Hydrochloride

In a 500 ml round bottom flask provided with efficient stirring and external cooling arrangement, 51 ml (, 0.5 mole) of conc. HCl was cooled to below 5 deg C and 25 gms (0.13 mole) 3-chloro-4-fluoroaniline was added. The hydrochloride thus precipitated was then diazotised below 0 deg C with 12 gms (0.17 mole)sodium nitrite and the resulting diazonium salt was decomposed with 100 gms (0.79 mole) sodium sulphite and 12 ml caustic lye. The reaction mixture was filtered to remove impurities.225 ml conc. HCl was added and stirred well and allowed to stand overnight. The 3-chloro-4-fluorophenylhydrazine hydrochloride thus precipitated was filtered and recrystallized from water. The dried product was 18 gms (yield 69%) M.pt: decomposed at 193 deg C. IR (KBr) cm−1 2939 and 2690(NH), 1506 (C=C), 1114 (C—F), 744(C—Cl)

Part B
Preparation of 1-(4-Methylphenyl)-4,4,4-Trifluorobutane-1,3 -Dione.

The preparation is described in Part B of example 1

Part C
Preparation of 1-(3-Chloro-4-Fluorophenyl)-5-(4-Methylphenyl)-3-(Trifluoromethyl)Pyrazole 15 gms (0.093 mole) of 3-chloro-4-fluorophenylhydrazine hydrochloride of Part A and 11 gms (0.048 mole) of 1-(4-Methylphenyl)-4,4,4-trifluorobutane -1,3-dione of Part B as given in example 1 was refluxed in 100 ml glacial acetic acid for 36 hours and then cooled to below 15 deg C and filtered. The residue was washed with hot water till neutral pH. The crude product (17 gms) was recrystallized from Methanol to give 10 gms (58% yield) M.pt: 77 deg C. The purity was 99.8% by HPLC IR (KBr) cm−1 at 1500 (C=C), 1470 (—C=NH ) 1242 (CF3), 1222(C—F), 1157 and 1128 (C—N), 808 (C—Cl)

The following compounds (examples 2A -a to 21 -a) was obtained according to procedures similar to that exemplified in PART A of Example 3. The appropriate aniline were used for the preparation of the phenylhydrazine hydrochloride intermediates and recrystallized in the similar manner as above:

2A-a) 3-Chlorophenylhydrazine hydrochloride
This intermediate was prepared by diazotisation of commercially available 3-Chloroaniline. The Hydrazine hydrochloride was recrystallized from water to give a light brown powder in 80% yield
M.pt: 215 deg C decomposes
IR (KBr) cm−1 at 3219 and 3006 (NH), 1602 (N-N), 1500 (C=C), 779(C—Cl)

2B-a) 4-Chlorophenylhydrazinehydrochloride
This intermediate was prepared by diazotisation of commercially available 4-Chloroaniline. The Hydrazine hydrochloride was recrystallized from water to give a light pinkish brown powder in 72% yield
M.pt: 205 deg C decomposes
IR (KBr) cm−1 at 3215 and 2989(NH) 1585 (N-N), 1496 (C=C), 648(C—Cl)

2C-a) 2,4-Difluorophenylhydrazine hydrochloride
This intermediate was prepared by diazotisation of commercially available 2,4-Difluoroaniline. The Hydrazine hydrochloride was recrystallized from water to give a light brown powder in 69% yield
M.pt: 215 deg C decomposes
IR (KBr) cm−1 2923 and 2667(NH), 1618 (NH), 1504 (aromatic C=C), 715 (C—Cl), 1286, 1099 (C—F)

2D-a) 3-fluorophenylhydrazine hydrochloride
This intermediate was prepared by diazotisation of commercially available 3-Fluoroaniline. The Hydrazine hydrochloride was recrystallized from water to give a light brown powder in 70% yield
M.pt: 237 deg C decomposes
IR (KBr) cm−1 3448 and 3199(NH), 1581 (NH), 1496 (C=C), 675(C—Cl), 1151, 1263 (C—F)

2E-a) 4-fluorophenylhydrazine hydrochloride
This intermediate was prepared by diazotisation of commercially available 4-Fluoroaniline. The Hydrazine hydrochloride was recrystallized from water to give a light yellow powder in 68% yield
M.pt: 180 deg C decomposes
IR (KBr) cm−1 3448 (NH), 1514 (NH), 1232, 1066 (C—F)

2F-a) 3,4-Dichlorophenylhydrazine hydrochloride
This intermediate was prepared by diazotisation of commercially available 3,4-Dichloroaniline. The Hydrazine hydrochloride was recrystallized from water to give a light cream powder in 66% yield
M.pt: 185 deg C decomposes
IR (KBr) cm−1 3618 and 3209(NH), 1614 (NH), 1475 (C=C), 671 (C—Cl)

2G-a) 2-Fluoro4-methylphenylhydrazine hydrochloride
This intermediate was prepared by diazotisation of commercially available 2-Fluoro-4-methylaniline. The Hydrazine hydrochloride was recrystallized from water to give a brown powder in 70% yield
M.pt: Above 300 deg C
IR (KBr) cm−1 3450(NH), 1637 (NH), 1137 (C—F).

2H-a) 2-Fluoro-5-Methylphenylhydrazine hydrochloride
This intermediate was prepared by diazotisation of commercially available 2-Fluoro-5-methylaniline. The Hydrazine hydrochloride was recrystallized from water to give a brown powder in 74% yield
M.pt: Above 300 deg C
IR (KBr) cm−1 3427(NH), 1617 (NH), 1150(C—F)

2I-a) 3-Fluoro-4-Methylphenylhydrazine hydrochloride
This intermediate was prepared by diazotisation of commercially available 3-Fluoro4-Methylaniline. The Hydrazine hydrochloride was recrystallized from water to give a light pinkish brown powder in 68% yield
M.pt: 195 deg C decomposes
IR (KBr) cm−1 3436 (NH), 1583 (NH), 1508 (C=C), 640 (C—Cl), 1232,1097 (C—F)

The following compounds (examples 2 A to 2 I) was prepared in the similar procedure as exemplified in the Part C of example 3 using the appropriate hydrochloride salt of hydrazino compounds:

2A) 1-(3-CHLOROPHENYL)-5-(4-METHYLPHENYL)-3-(TRIFLUOROMETHYL) PYRAZOLE.
Yield: 42%
A white crystalline powder.
M.pt: 45 deg C
Purity by HPLC : 98.86%
IR (KBr) cm–1 at 1595(C=C), 1471 (—C=NH), 1232 (CF3), 1157 and 1128 (C—N ), 806 (C—Cl)

2B) 1-(4-CHLOROPHENYL)-5-(4-METHYLPHENYL)-3-(TRIFLUOROMETHYL) PYRAZOLE.
Yield: 57%
A white crystalline powder
M.pt: 126 deg C
Purity by HPLC: 97.9%
IR (KBr) cm–1 at 1496(C=C), 1471 (—C=NH ) 1234 (CF3), 1159 and 1134 (C—N), 806(C—Cl)

2C) 1-(2,4-DIFLUOROPHENYL)-5-(4-METHYLPHENYL)-3-(TRIFLUOROMETHYL) PYRAZOLE
Yield: 36%
A creamish white crystalline powder.
M.pt: 83 deg C
Purity by HPLC: 99.95%
IR (KBr) cm–1 shows absorption/cm at 1509 (C=C), 1471 (—C=NH) 1246 (CF3) 1093(C—F), 1134(C—N)

2D) 1-(3-FLUOROPHENYL)-5-(4-METHYLPHENYL)-3-(TRIFLUOROMETHYL) PYRAZOLE.
Yield: 38%
A white crystalline powder.
M.pt: 58 deg C
Purity by HPLC: 97.96%
IR (KBr) cm–1 at 1602(C=C), 1471 (—C=NH ) 1244 (CF3), 1161 and 1128 (C—N)

2E) 1-(4-FLUOROPHENYL)-5-(4-METHYLPHENYL)-3-(TRIFLUOROMETHYL) PYRAZOLE.
Yield: 6%
A brown solid.
M.pt: 68–70deg C
IR (KBr) cm–1 at 1604 (C=C), 1477 (—C=NH ) 1248 (CF3), 1159 and 1130 (C—N), 2F) 1-(3,4-DICHLOROPHENYL)-5-(4-METHYLPHENYL)-3-(TRIFLUOROMETHYL)-PYRAZOLE.
Yield: 31%
A light brown colored powder.
M.pt: 94 deg C
Purity by HPLC: 98.86%
IR (KBr) cm–1 at 1591(C=C ), 1471 (—C=NH ) 1232 (CF3), 1159 and 1136 (C—N), 817 (C—Cl)

2G) 1 -(2-FLUORO-4-METHYLPHENYL)-5-(4-METHYLPHENYL)-3-(TRIFLUOROMETHYL) PYRAZOLE.
Yield: 80%
A pale brown colored liquid
B.P.: 145deg C
Purity by HPLC: 99.6%
IR (KBr) cm–1 at 1580(C=C), 1468 (—C=NH ) 1228 (CF3), 1145 and 1139 (C—N)

2H) 1-(2-FLUORO-5-METHYLPHENYL)-5-(4-METHYLPHENYL)-3-(TRIFLUOROMETHYL) PYRAZOLE.
Yield: 40%
A light brown colored product
M.pt: 45 deg C IR (KBr) cm–1 at 1600 (C=C ), 1470 (—C=NH ) 1230 (CF3), 1150 and 1125 (C—N), 2I) 1 -(3-FLUORO-4-METHYLPHENYL)-5-(4-METHYLPHENYL)-3-(TRIFLUOROMETHYL) PYRAZOLE.
Yield: 80%
A brown colored viscous oil.
B.P.: 144 deg C
IR (KBr) cm–1 at 1595(C=C), 1471. (—C=NH ) 1232 (CF3), 1157 and 1128 (C—N), Biological Evaluation The test compounds of formula 1 and 2 were evaluated for anti-inflammatory activity and ulcerogenic activity.

Wistar rats (120–180 gms ) were fasted overnight and were given per oral either vehicle (1% sodium CMC in water) or a test compound. The paw volume was measured using a Plethysmometer, (UGO- Basile Italy) based on the principal of water displacement. The animals were then injected subcutaneously with 0.1 ml of 1% w/v of Carrageenan suspension in to the plantar tissue of the right hind paw. The paw volume was measured at 0 hour and subsequently at 1 hour intervals upto 6 hours. The percent increase in the paw volume was compared with the test compound and control. The difference of the average values between treated and control groups was calculated for each time interval and statistically evaluated. The animals were sacrificed and the stomach of each animal was removed, a longitudinal incision along the greater curvature was made and the presence and absence of gastric irritation was determined. All the treatment groups were coded to eliminate observer's bias. The results indicate that some of the test compounds exhibits anti-inflammatory activity comparable with known NSAIDS and these compounds also revealed mild injury which was significantly less than the ulcerogenic index of standard NSAID known to cause gastric lesions.

It is to be understood that various modifications or changes that may be made to that described herein above by those of ordinary skill in the art are also contemplated by the present invention and are to be included within the spirit and purview of this application and the following claims:

We claim:

1. A compound for the treatment of inflammation and other related disorders having the general formula:

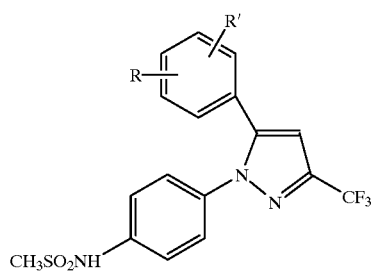

or a pharmaceutically acceptable salt thereof, wherein R is selected from the group consisting of ethyl, methyl, ethoxy, methoxy, chloro, and carboxyl, and wherein R' is selected from the group consisting of hydrogen, methyl, and chloro.

2. A compound as claimed in claim 1, selected from the group consisting of:

i. N-[4-[5-(4-Methylphenyl)-3-(trifluoromethyl)-1H-pyrazol-1-yl]phenyl]methanesulphonamide;

ii. N-[4-[5-(4-Ethylphenyl)-3-(trifluoromethyl)-1H-pyrazol-1-yl]phenyl]methanesulphonamide;

iii. N-[$^4$-[$^5$-(4-Methoxyphenyl)-3-(trifluoromethyl)-1H-pyrazol-1-yl]phenyl]methanesulphonamide;

iv. N-[4-[5-(4-Ethoxyphenyl)-3-(trifluoromethyl)-1H-pyrazol-1-yl]phenyl]methanesulphonamide;

V. N-[⁴-[5-(3,4-Dichlorophenyl)-3-(trifluoromethyl)-1H-pyrazol-1-yl]phenyl]methanesulphonamide;

vi. N-[4-[5-(2,4-Dichlorophenyl)-3-(trifluoromethyl)-1H-pyrazol-1-yl]phenyl]methanesulphonamide;

vii. N-[4-[5-(2-Methylphenyl)3-(trifluoromethyl)-1H-pyrazol-1-yl]phenyl]methanesulphonamide;

viii. N-[4-[5-(2,4-Dimethylphenyl)-3-(trifluoromethyl)-1H-pyrazol-1-yl]phenyl]methanesulphonamide;

ix. N-[4-[5-(3,4-Dimethylphenyl)-3-(trifluoromethyl)-1H-pyrazol-1-yl]phenyl]methanesulphonamide;

x. 4-[1-[4-(Methanesulphonylamido)phenyl]-3-(trifluoromethyl)-1H-pyrazol-5-yl]benzoic acid; and xi. 2-[1-[⁴-(Methanesulphonylamido)phenyl]-3-(trifluoromethyl)-1H-pyrazol-5-yl]benzoic acid.

3. A compound for the treatment of inflammation and other related disorder of the general formula:

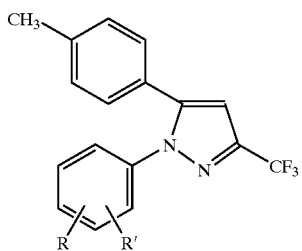

or a pharmaceutically acceptable salt thereof, wherein R is chloro or fluoro, and wherein R' is selected from the group consisting of hydrogen, fluoro, chloro, and methyl.

4. A compound as claimed in claim 3, selected from the group consisting of:

i. 1-(3-Chloro-4-fluorophenyl)-5-(4-methylphenyl)-3-(trifluoromethyl) pyrazole;

ii. 1-(3-Chlorophenyl)-5-(4-methylphenyl)-3-(trifluoromethyl)pyrazole;

iii. 1-(4-Chlorophenyl)-5-(4-methylphenyl)-3-(trifluoromethyl)pyrazole;

iv. 1-(2,4-Difluorophenyl)-5-(4-methylphenyl)-3-(trifluoromethyl) pyrazole;

v. 1-(3-Fluorophenyl)-5-(4-methylphenyl)-3-(trifluoromethyl)pyrazole;

vi. 1-(4-Fluorophenyl)-5-(4-methylphenyl)-3-(trifluoromethyl)pyrazole;

vii. 1-(3,4-Dichlorophenyl)-5-(4-methylphenyl)-3-(trifluoromethyl) pyrazole;

viii. 1-(2-Fluoro-4-methylphenyl)-5-(4-methylphenyl)-3-(trifluoromethyl) pyrazole;

ix. 1-(2-Fluoro-5-methylphenyl)-5-(4-methylphenyl)-3-(trifluoromethyl) pyrazole; and x. 1-(3-Fluoro-4-methylphenyl)-5-(4-methylphenyl)-3-(trifluoromethyl) pyrazole.

5. A pharmaceutical composition or a formulation or any other drug delivery system comprising a pharmaceutically acceptable carrier or diluent containing a therapeutically effective amount of the compound as claimed in claim 1, or a pharmaceutically acceptable salt thereof.

6. A pharmaceutically acceptable composition for treating an inflammatory condition susceptible to treatment with an NSAID agent comprising a non-toxic therapeutically effective amount of a compound as claimed in claim 1 and a pharmaceutically acceptable carrier or diluent in association with a further analgesic medicament.

7. A pharmaceutical composition for treating an inflammatory condition susceptible to treatment with an NSAID agent comprising a non-toxic therapeutically effective amount of a compound having the general formula:

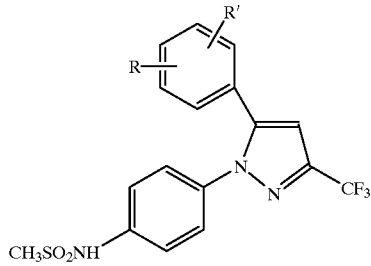

or a pharmaceutically acceptable salt thereof, wherein R and R' are selected from the group consisting of: alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-arylsulfamyl, cyanoamido, amino, amidino, N-monoalkylamido, N-monoarylamido, N,N-dialkylamido, N-alkyl-N-arylamido, N,N,-dialkylsulfamyl, and combinations thereof, and wherein the alkyl or alkyl-portions of R and R' have 1 to 3 carbon atoms; and a pharmaceutically acceptable carrier or diluent in association with an analgesic medicament, the composition being in a form selected from the group consisting of: parenteral, oral, sublingual, rectal, vaginal, topical, transdermal, ocular, intranasal, aerosol, and combinations thereof.

8. A method for treatment or prevention of inflammation and associated disorders in a patient comprising the step of administering a therapeutically effective amount of a compound of claim 1.

9. A compound selected from the group consisting of: N-[4-[5-(2,4-Dimethylphenyl)-3(trifluoromethyl)1H-pyrazole-1-yl]phenyl]methanesulphonamide, pharmaceutically acceptable salts of N-[4-[5-(2,4-Dimethylphenyl)-3 (trifluoromethyl)1H-pyrazole-1-yl]phenyl] methanesulphonamide, and combinations thereof.

10. A compound selected from the group consisting of: 1-(3-Chloro-4-fluorophenyl)-5-(4-methylphenyl)-3-(trifluoromethyl)pyrazole and its pharmaceutically acceptable salts, 1-(2-Fluoro-4-methylphenyl)-5-(4-methylphenyl)-3-(trifluoromethyl)pyrazole and its pharmaceutically acceptable salts, and combinations thereof.

11. A pharmaceutical composition or a formulation or any other drug delivery system comprising a pharmaceutically acceptable carrier or diluent containing a therapeutically effective amount of the compound as claimed in claim 3, or a pharmaceutically acceptable salt thereof.

12. A pharmaceutically acceptable composition for treating an inflammatory condition susceptible to treatment with an NSAID agent comprising a non-toxic therapeutically effective amount of a compound as claimed in claim 3 and a pharmaceutically acceptable carrier or diluent in association with a further analgesic medicament.

13. A method for treatment or prevention of inflammation and associated disorders in a patient comprising the step of administering a therapeutically effective amount of the compound of claim 3.

14. A pharmaceutical composition for treating an inflammatory condition susceptible to treatment with an NSAID agent comprising a non-toxic therapeutically effective amount of a compound having the general formula:

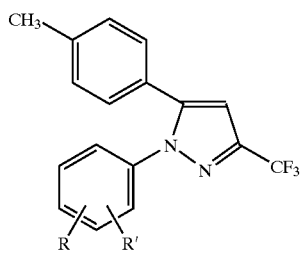

or a pharmaceutically acceptable salt thereof, wherein R and R' are selected from the group consisting of: alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-arylsulfamyl, cyanoamido, amino, amidino, N-monoalkylamido, N-monoarylamido, N,N-dialkylamido, N-alkyl-N-arylamido, N,N,-dialkylsulfamyl, and combinations thereof, and wherein the alkyl or alkyl-portions of R and R' have 1 to 3 carbon atoms; and
a pharmaceutically acceptable carrier or diluent in association with an analgesic medicament,
the composition being in a form selected from the group consisting of: parenteral, oral, sublingual, rectal, vaginal, topical, transdermal, ocular, intranasal, aerosol, and combinations thereof.

15. A pharmaceutical composition for treating an inflammatory condition susceptible to treatment with an NSAID agent comprising a non-toxic therapeutically effective amount of a compound having the general formula:

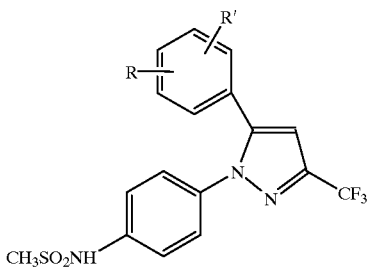

or a pharmaceutically acceptable salt thereof, wherein R and R' are selected from the group consisting of: alkyl, hydrogen, chlorine, bromine, iodine, astatine, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-arylsulfamyl, cyanoamido, amino, amidino, N-monoalkylamido, N-monoarylamido, N,N-dialkylamido, N-alkyl-N-arylamido, N,N,-dialkylsulfamyl, and combinations thereof, and wherein the alkyl or the alkyl-portions of R and R' have 1 to 3 carbon atoms.

16. The composition of claim 15, further comprising an analgesic.

17. A method for treatment or prevention of inflammation and associated disorders in a patient comprising the step of administering a therapeutically effective amount of a compound according to claim 15.

18. A pharmaceutical composition for treating an inflammatory condition susceptible to treatment with an NSAID agent comprising:

a non-toxic therapeutically effective amount of a compound having the general formula:

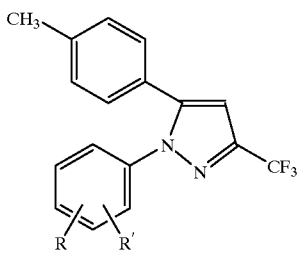

or a pharmaceutically acceptable salt thereof, wherein R and R' are selected from the group consisting of: alkyl, hydrogen, halogens, haloalkyl, cyano, nitro, formyl, carboxyl, alkoxycarbonyl, carboxyalkyl, alkoxycarbonylalkyl, hydroxyalkyl, alkylthio, alkylsulfinyl, alkylsulphonyl, N-alkylsulfamyl, N-arylsulfamyl, cyanoamido, amino, amidino, N-monoalkylamido, N-monoarylamido, N,N-dialkylamido, N-alkyl-N-arylamido, N,N,-dialkylsulfamyl, and combinations thereof, and wherein the alkyl or alkyl-portions of R and R' have 1 to 3 carbon atoms; and an analgesic.

* * * * *